US012599575B2

(12) United States Patent
Kim et al.

(10) Patent No.: US 12,599,575 B2
(45) Date of Patent: Apr. 14, 2026

(54) ANTIMICROBIAL ADJUVANT CONTAINING BIPHENYL DERIVATIVE COMPOUND AS ACTIVE INGREDIENT, AND USES THEREOF

(71) Applicant: KOREA RESEARCH INSTITUTE OF BIOSCIENCE AND BIOTECHNOLOGY, Daejeon (KR)

(72) Inventors: Jun-Seob Kim, Daejeon (KR); Choong-Min Ryu, Daejeon (KR); Seon-Yeong Kim, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 419 days.

(21) Appl. No.: 18/275,475

(22) PCT Filed: Jan. 28, 2022

(86) PCT No.: PCT/KR2022/001632
§ 371 (c)(1),
(2) Date: Aug. 2, 2023

(87) PCT Pub. No.: WO2022/169243
PCT Pub. Date: Aug. 11, 2022

(65) Prior Publication Data

US 2024/0148670 A1 May 9, 2024

(30) Foreign Application Priority Data

Feb. 2, 2021 (KR) ........................ 10-2021-0014932

(51) Int. Cl.

| | |
|---|---|
| ***A61K 31/06*** | (2006.01) |
| ***A01N 43/713*** | (2006.01) |
| ***A01N 63/25*** | (2020.01) |
| ***A61K 31/085*** | (2006.01) |
| ***A61K 31/12*** | (2006.01) |
| ***A61K 31/343*** | (2006.01) |
| ***A61K 31/353*** | (2006.01) |
| ***A61K 31/4035*** | (2006.01) |
| ***A61K 38/12*** | (2006.01) |
| ***A61P 1/00*** | (2006.01) |
| ***A61P 31/04*** | (2006.01) |
| ***A61P 43/00*** | (2006.01) |

(52) U.S. Cl.
CPC .............. *A61K 31/06* (2013.01); *A61K 38/12* (2013.01); *A61P 31/04* (2018.01)

(58) Field of Classification Search
CPC ...... A61K 31/06; A61K 31/085; A61K 31/12; A61K 31/353; A61K 31/4035; A61K 38/12; A61K 2300/00; A61P 1/00; A61P 31/04; A61P 43/00; A01N 43/713; A01N 63/25; A01N 33/22; Y02A 50/30
See application file for complete search history.

(56) References Cited

U.S. PATENT DOCUMENTS

| | | | | |
|---|---|---|---|---|
| 2005/0065220 | A1* | 3/2005 | Heiman ................. | A01N 33/22 514/728 |
| 2014/0323763 | A1 | 10/2014 | Furkert et al. | |
| 2015/0272910 | A1 | 10/2015 | Clement et al. | |
| 2016/0222061 | A1 | 8/2016 | Brown et al. | |
| 2017/0073373 | A1 | 3/2017 | Brown et al. | |
| 2017/0348383 | A1 | 12/2017 | Coates et al. | |
| 2019/0321441 | A1 | 10/2019 | Coates et al. | |
| 2020/0197480 | A1 | 6/2020 | Coates et al. | |
| 2021/0221848 | A1 | 7/2021 | Brown et al. | |
| 2023/0322858 | A1 | 10/2023 | Brown et al. | |

FOREIGN PATENT DOCUMENTS

| | | | |
|---|---|---|---|
| EP | 0 027 679 | A2 | 4/1981 |
| JP | 2016-527186 | A | 9/2016 |
| JP | 2018-503614 | A | 2/2018 |
| KR | 10-2016-0009041 | A | 1/2016 |
| KR | 10-2016-0135739 | A | 11/2016 |
| KR | 10-2018-0106599 | A | 10/2018 |
| KR | 10-2018-0119890 | A | 11/2018 |
| WO | 2012/085092 | A | 6/2012 |
| WO | 2016/097754 | A | 6/2016 |
| WO | 2018/224843 | A1 | 12/2018 |

OTHER PUBLICATIONS

Extended European Search Report dated Jun. 13, 2024, issued in European Application No. 22749992.8.
Communication dated Jul. 23, 2024, issued in Japanese Application No. 2023-546500.
Felpin et al., "Improved Suzuki-Miyaura Reactions of Aryldiazonium Salts with Boronic Acids by Tuning Palladium on Charcoal Catalyst Properties", Adv. Synth. Catal., 2009, vol. 351, pp. 649-655 (7 pages).
Barlin et al., "Potential Antimalarials. XVI* 4'-Chloro-3-[7"-chloro(and trifluoromethyl)quinolin-4"-yl]amino-5-(substituted amino)methylbiphenyl-4-ols and 4'-Bromo(and 3'-trifluoromethyl)-3-(substituted amino)methyl-5-(7"-trifluoromethylquinolin-4"-yl)aminobiphenyl-2-ols", Aust. J. Chem., 1992, vol. 45, pp. 1845-1855 (11 pages).
Communication dated Aug. 13, 2024, issued in Korean Application No. 10-2022-0013425.

(Continued)

*Primary Examiner* — Kamal A Saeed
*Assistant Examiner* — Sagar Patel
(74) *Attorney, Agent, or Firm* — Sughrue Mion, PLLC

(57) ABSTRACT

The present invention relates to an antimicrobial adjuvant containing a biphenyl derivative compound as an active ingredient, and a technology of various uses thereof. The compound of the present invention reduces the dosage of polymyxin antibiotics, which are administered to inhibit the proliferation of gram-negative bacteria, by enhancing the sensitivity of the gram-negative bacteria with respect to the polymyxin antibiotics, is concomitantly administered with the polymyxin antibiotics to show gram-negative bacteria growth inhibitory and killing effects, may notably reduce side effects such as nephrotoxicity, and may prevent or treat sepsis and septic shock due to antibiotic overuse.

14 Claims, 11 Drawing Sheets

(56) References Cited

OTHER PUBLICATIONS

Malathy Krishnamurthy et al., "Enhancing the antibacterial activity of polymyxins using a nonantibiotic drug", Infection and Drug Resistance, 2019, pp. 1393-1405, vol. 12.
Shawn Zimmerman et al., "A Whole-Cell Screen Identifies Small Bioactives That Synergize with Polymyxin and Exhibit Antimicrobial Activities against Multidrug-Resistant Bacteria", Antimicrobial Agents and Chemotherapy, Mar. 2020, pp. 1-18, vol. 64, No. 3.
Yuan Liu et al., "Antibiotic adjuvants: an alternative approach to overcome multi-drug resistant Gram-negative bacteria", Critial Reviews in Microbiology, 2019, 15 pgs.
Ronald A. Dixon et al., "Polymyxin B and polymyxin B nonapeptide alter cytoplasmic membrane permeability in *Escherichia coli*", Journal of Antimicrobial Chemotherapy, 1986, pp. 557-563, vol. 18.
K. Muddukrishnaiah, "Synthesis, Characterization, and In vitro Antibacterial Activity and Molecular Docking Studies of N4, N4'-Dibutyl-3,3'-Dinitro-[1,1-Biphenyl]-4,4-Diamine", Biomedical and Biotechnology Research Journal, 2020, pp. 318-322, vol. 4, No. 4.
Paulo R. Ribeiro et al., "A new biphenyl and antimicrobial activity of extracts and compounds from Clusia burlemarxii", Fitoterapia, 2011, pp. 1237-1240, vol. 82.
Malvika Kaul et al., "A Bactericidal Guanidinomethyl Biaryl That Alters the Dynamics of Bacterial FtsZ Polymerization", Journal of Medicinal Chemistry, 2012, pp. 10160-10176, vol. 55.
International Search Report for PCT/KR2022/001632 dated, May 10, 2022 (PCT/ISA/210).

* cited by examiner

ANTIMICROBIAL ADJUVANT CONTAINING BIPHENYL DERIVATIVE COMPOUND AS ACTIVE INGREDIENT, AND USES THEREOF

CROSS REFERENCE TO RELATED APPLICATIONS

This application is a National Stage of International Application No. PCT/KR2022/001632 filed Jan. 28, 2022, claiming priority based on Korean Patent Application No. 10-2021-0014932 filed Feb. 2, 2021, the entire disclosures of which are incorporated herein by reference.

TECHNICAL FIELD

The present invention relates to an antimicrobial adjuvant including a biphenyl derivative compound as an effective component and a technology variously using the compound.

BACKGROUND ART

Emergence and rise of antibiotic-resistant bacteria which acquires drug resistance to survive even when exposed to antibiotics are causing big problems all over the world. As of 2018, the number of deaths from infections with antibiotic-resistant bacteria worldwide reached 700,000, and in the Republic of Korea, since infections with five representative antibiotic-resistant bacteria (methicillin-resistant *Staphylococcus aureus* (MRSA), multidrug-resistant *Acinetobacter baumannii* (MDRA), multidrug-resistant *Pseudomonas aeruginosa* (MRPA), Vancomycin-resistant enterococci (VRE), and carbapenem-resistant Enterobacteriaceae (CRE)) resulted in 9,000 infections and deaths reaching 3,600 in one year, the mortality rate was found to be about 40%. In addition, since the total social cost in the Republic of Korea due to productivity loss resulting from medical expenses, nursing expenses, and premature death of patients infected with antibiotic-resistant bacteria is estimated to be 5500 billion Korean won per year, the spread of antibiotic resistance may cause economic loss as well as loss of human health. In particular, due to the emergence of multidrug-resistant bacteria (referred to as "super-bacteria") which are resistant to all existing antibiotics at the same time, damage caused by antibiotic-resistant bacteria is expected to grow exponentially.

It is known that the antibiotic-resistant bacteria acquire resistance to antibiotics by obtaining the resistance-related gene for corresponding mechanisms ① producing an antibiotic degrading enzyme to inactivate antibiotics or changing the structure of antibiotics by an antibiotic converting enzyme, ② activating antibiotic outflow through an antibiotic inflow suppression/discharge pump to lower an intracellular antibiotic concentration, ③ changing a target protein to which an antibiotic binds by mutation, or the like. The antibiotic-resistant bacteria effectively resist antibiotics by mobilizing two or more of resistance mechanisms, and it is known that as the more mechanisms are mobilized, a resistance degree is increased. Therefore, an antibiotic against resistant strains should ① inhibit a hitherto unknown new bacteria target or ② avoid development of resistance through inhibition of various target groups.

In order to solve the problem of the antibiotic-resistant bacteria infections, development of novel antibiotics is needed, but it is difficult to excavate a target for novel drug development, and it costs about 800 million dollars on average and takes at least 10 years for novel drug development, which causes a lot of difficulties. A more serious problem is that though a new antibiotic is developed by excavating a novel target which may avoid resistance mechanisms known so far, resistant bacteria will rapidly emerge. In reality, linezolid, which has a mechanism of action different from conventional antibiotics, was approved as the only novel target inhibitor in the 2000s, but bacteria resistant thereto have already appeared. Therefore, in terms of cost and time, developing a substance which may inhibit a resistance mechanism acquired by antibiotic-resistant bacteria so that the effectiveness of existing antibiotics may be increased may be an effective strategy for coping with infection with antibiotic-resistant bacteria, rather than developing a novel antibiotic.

Thus, development of a technology to kill bacteria by increasing susceptibility to antibiotics by a treatment concurrently with an antibiotic which becomes unusable due to resistance is more needed.

DISCLOSURE OF THE INVENTION

Technical Problem

The present invention has been made to solve the problems of the conventional art, and provides an antimicrobial adjuvant which improves bacterial susceptibility to antibiotics.

In addition, another objective of the present invention is to provide an antimicrobial composition including the antimicrobial adjuvant described above and a polymyxin-based antibiotic as effective components.

In addition, still another objective of the present invention is to provide a pharmaceutical composition for preventing or treating organ damage from sepsis or septic shock including the antimicrobial adjuvant described above and a polymyxin-based antibiotic as effective components.

Technical Solution

In order to achieve the above objectives, an aspect of the present invention provides an antimicrobial adjuvant including a compound represented by the following Chemical Formula 1 or a pharmaceutically acceptable salt thereof as an effective component.

[Chemical Formula 1]

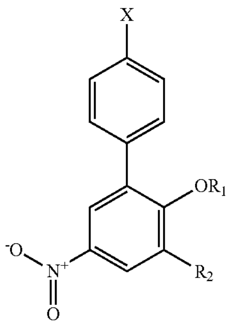

wherein X is a halogen atom, and $R_1$ and $R_2$ are independently of each other a hydrogen atom or alkyl having 1 to 6 carbon atoms.

In addition, another aspect of the present invention provides an antimicrobial composition including the antimicrobial adjuvant and a polymyxin-based antibiotic as effective components.

In addition, still another aspect of the present invention provides a pharmaceutical composition for preventing or treating organ damage from sepsis or septic shock including the antimicrobial adjuvant described above and a polymyxin-based antibiotic as effective components.

Advantageous Effects

The antimicrobial adjuvant of the present invention improves sensitivity of gram-negative bacteria to a polymyxin-based antibiotic, thereby reducing a dosage of the polymyxin-based antibiotic treated for inhibiting gram-negative bacterial growth by up to 128 times.

In addition, the antimicrobial adjuvant of the present invention is administered in combination with a polymyxin-based antibiotic to cause a synergistic effect, thereby showing an effect of inhibiting gram-negative bacterial growth and killing gram-negative bacteria.

In addition, according to the present invention, conventional side effects such as nephrotoxicity caused by overdose of polymyxin may be significantly lowered and sepsis and septic shock caused by overuse of antibiotics may be prevented or treated.

The effect of the present invention is not limited to the effects mentioned above, and other effects which are not mentioned herein may be clearly understood by a person skilled in the art from the following description.

MODE FOR CARRYING OUT THE INVENTION

Figure 1:
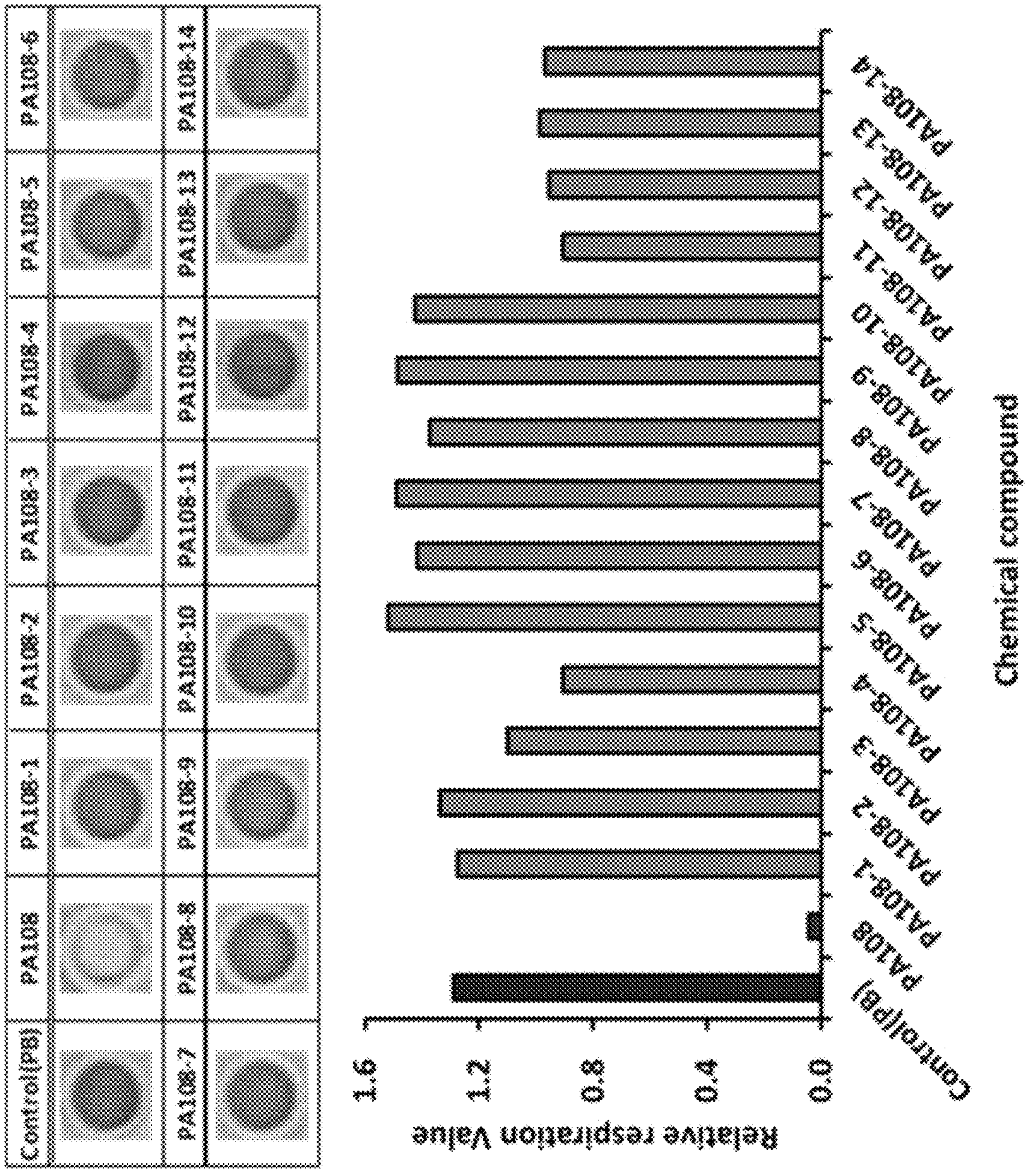
FIG. 1 is a graph showing a bacterial growth inhibitory effect of PA108 and its derivatives (PA108-1 to 14) and polymyxin B (PMB) on *Acinetobacter baumannii* strains through a bacterial relative respiration rate.

Hereinafter, the present invention will be described in detail.

An aspect of the present invention provides an antimicrobial adjuvant which improves bacterial susceptibility to antibiotics.

The antimicrobial adjuvant of the present invention includes a compound represented by the following Chemical Formula 1 or a pharmaceutically acceptable salt thereof as an effective component:

[Chemical Formula 1]

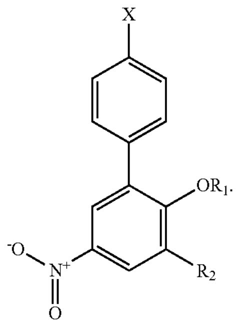

In Chemical Formula 1, X may be any one halogen atom selected from the group consisting of F, Cl, Br, and I, X may be any one selected from the group consisting of F, Cl, and Br, or X may be Cl.

In Chemical Formula 1, $R_1$ and $R_2$ may be independently of each other a hydrogen atom or alkyl.

The alkyl refers to a straight chain or branched saturated aliphatic hydrocarbon group, may be alkyl having 1 to 12, 1 to 10, 1 to 8, or 1 to 6 carbon atoms, and for example, may be methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, or the like.

In addition, the alkyl may be substituted or unsubstituted. When the alkyl is substituted, the substituent(s) may be substituted at any possible connection point. The substituent (s) may be preferably any one or more independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo, carboxy, and alkoxycarbonyl, but is (are) not limited thereto.

A "pharmaceutically acceptable salt" refers to a salt prepared by a conventional method, and the salt includes inorganic acids and organic acids and may be any one selected from the group consisting of hydrochloric acid, hydrobromic acid, sulfuric acid, phosphoric acid, methanesulforic acid, ethanesulforic acid, malic acid, acetic acid, oxalic acid, tartaric acid, citric acid, lactic acid, furmaric acid, succinic acid, maleic acid, salicylic acid, benzoic acid, phenylacetic acid, and mandelic acid, but is not limited thereto.

The "pharmaceutically acceptable salt" also includes those formed from cations such as sodium, potassium, aluminum, calcium, lithium, magnesium, and zinc and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazien, tri(hydroxymethyl)aminomethane, and tetramethylammoniumhydroxide. These salts may be prepared by a standard procedure, for example, a reaction of a free acid with an appropriate organic base or inorganic base. The "pharmaceutically acceptable salt" also includes free acid, free base, and zwitterionic forms.

The compound represented by Chemical Formula 1 may have an effect of improving the susceptibility of antibiotic-resistant bacteria to the antibiotics. Therefore, the compound represented by Chemical Formula 1 may be used as an effective component of an antimicrobial adjuvant which may be treated in combination with an antibiotic against bacteria resistant to the antibiotic.

The "antimicrobial adjuvant" is also referred to as a "antibiotic adjuvant" and refers to a substance which does not directly kill bacteria, but increases bacterial susceptibility to an antibiotic by inhibiting bacterial resistance to the antibiotic, inducing intracellular accumulation of the antibiotic, or the like.

An "antibiotic" generally refers to a substance having antimicrobial activity, and for example, may be any one or more selected from the group consisting of penicillins, cephalosporins, monobactams, and carbapenems which are beta-lactam-based antibiotics having a beta-lactam ring as a basic structure, polymyxins which change bacterial cell membrane permeability to show an antimicrobial effect, aminoglycosides which move to a periplasmic space through porin in the outer membrane of gram-negative bacteria and then move into cells to show an antimicrobial effect, macrolides which binds to 50S of bacterial ribosome to inhibit protein synthesis to show an antimicrobial effect, tetracyclines which show an antimicrobial effect on various kinds of bacteria and are known as broad spectrum antibiotics, glycopeptides which inhibit bacterial cell wall biosynthesis to show an antimicrobial effect, lincomycins which are separated in *Streptomyces lincolnensis* and has good antimicrobial power to anaerobic bacteria, quinolones which interfere with bacterial DNA replication to show an antimicrobial effect, combinations thereof, and derivatives thereof, and in particular, may be a polymyxin-based antibiotic.

The polymyxin-based antibiotic is a peptide antibiotic composed of a positively-charged huge ring and is composed of a heptapeptide ring and three amino acid tails connected to an aliphatic acid. In addition, the polymyxin-based antibiotic is produced by a non-ribosomal peptide synthase system in gram-negative bacteria such as *Paenibacillus polymyxa*, and has activity to bind to phospholipids present in an extracellular membrane of many gram-negative bacteria to activate phospholipase to destroy the cell membrane. The polymyxin-based antibiotic may be polymyxin A, polymyxin B, polymyxin C, polymyxin D, and polymyxin E (colistin), and, in particular, polymyxin B or polymyxin E having B1 ($C_{56}H_{98}N_{16}O_{13}$, molecular weight: 1203.49) and B2 ($C_{55}H_{96}N_{16}O_{13}$, molecular weight: 1189.47) as main components. The polymyxin B and the polymyxin E have the same structure except that an amino acid connected to position 6 is different in phenylalanine (Phe) and Leucine (Leu), respectively.

The bacteria may be included without limitation as long as they are gram-negative bacteria having an outer membrane, and specifically, may be pathogenic gram-negative bacteria, and for example, *Escherichia* sp., *Acinetobacter* sp., *Pseudomonas* sp., *Klebsiella* sp., and the like. Specifically, the *Escherichia* sp. includes *Escherichia coli, Escherichia albertii, Escherichia blattae, Escherichia fergusonii, Escherichia hermannii, Escherichia vulneris*, and the like, but is not limited thereto. The *Acinetobacter* sp. includes *Acinetobacter baumannii, Acinetobacter junii, Acinetobacter boissieri, Acinetobacter calcoaceticus, Acinetobacter haemolyticus, Acinetobacter nosocomialis, Acinetobacter schindleri, Acinetobacter ursingii*, and the like, but is not limited thereto. The *Pseudomonas* sp. includes *Pseudomonas aeruginosa; Pseudomonas fluorescens, Pseudomonas putida, Pseudomonas chlororaphis, Pseudomanas pertucinogena, Pseudomanas stutzeri, Pseudomanas syringae*, and the like, but is not limited thereto. The *Klebsiella* sp. includes *Klebsiella pneumonia, Klebsiella granulomatis, Klebsiella oxytoca, Klebsiella terrigena*, and the like, but is not limited thereto.

In particular, the bacteria may show resistance to antibiotics, in particular, at least one of the antibiotics described above. The "antibiotic-resistant bacteria" refer to bacteria which are not affected any more or hardly affected by at least one antibiotic which was previously effective, and mean that the bacteria have ability to resist antibiotics which previously had effective antimicrobial activity. The antibiotic-resistant bacteria may pass the ability to resist to offspring. The antibiotic-resistance mechanisms are various. For example, resistance may be shown by an impermeability mechanism to physically prevent antibiotics from reaching the inside of bacteria or an action site on bacteria, an outflow mechanism to prevent an effective amount of antibiotics from reaching the inside of bacteria or an action site on bacteria by rapidly removing the antibiotics from bacteria, a metabolic mechanism to destroy antibiotics, convert antibiotics into a harmless (or less harmful) compound, or more easily discharge compounds, or a bypass mechanism of using a pathway other than those of inhibiting bacteria by antibiotics, or through bacteria in the form of an antibiotic target (e.g., enzyme) which is less sensitive to antibiotics or bacteria having no target.

In addition, the antibiotic-resistant bacteria may have resistance to two or more antibiotics, which are also referred to as multidrug-resistant bacteria. The multidrug-resistant bacteria include, for example, Methicillin-susceptible *Staphylococcus aureus* (MSSA), Methicillin-resistant *Staphylococcus aureus* (MRSA), Vancomycin-Resistant *Staphylococcus aureus* (VRSA), Vancomycin-intermediate *Staphylococcus aureus* (VISA), Vancomycin-resistant enterococci (VRE), Vancomycin-susceptible enterococci (VSE), multidrug-resistant *Pseudomonas aeruginosa* (MRPA), Carbapenem-resistant *Pseudomonas aeruginosa* (CRPA), Carbapenem-resistant *Acinetobacter baumannii* (CRAB), Carbapenem-resistant Enterobacteriaceae (CRE), and the like.

In the specific example of the present invention, it was confirmed that when bacteria which conventionally show resistance to a polymyxin-based antibiotic are treated with the compound represented by Chemical Formula 1 at a concentration which does not have antimicrobial activity by itself in combination with polymyxin, death of the bacteria resistant to a polymyxin-based antibiotic is further promoted. Form the above result, it is clearly shown that the compound represented by Chemical Formula 1 further improves the susceptibility of antibiotic-resistant bacteria and may be used as an effective component of an antimicrobial adjuvant which may recover the antimicrobial activity of antibiotics.

Another aspect of the present invention provides an antimicrobial composition including an antimicrobial adjuvant including the compound represented by Chemical Formula 1 as an effective component and an antibiotic, as effective components.

As described above, since the compound represented by Chemical Formula 1 of the present invention has an effect of improving the susceptibility of an antibiotic-resistant bacteria to an antibiotic, the antimicrobial adjuvant described above is used in combination with an antibiotic, thereby recovering the conventional antimicrobial activity of an antibiotic.

When the antimicrobial composition of the present invention is administered to an antibiotic-resistant bacteria, expression of genes involved in zinc ion binding, identical protein binding, and ferric ion binding and expression of genes involved in peroxidase activity may be significantly decreased, and expression of genes involved in transport of substances through a cell membrane, in particular, ATPase-coupled sulfate transmembrane transporter activity may be significantly increased.

The antimicrobial composition of the present invention may change the environment inside and outside a bacterial cell membrane and destroy the integrity of the lipid bilayer region of the cell membrane to derive high depolarization of the cell membrane, thereby breaking cytoplasmic homeostasis and decreasing cell permeability to derive cell death.

The antibiotic-resistant bacteria are as described above, and in particular, may be gram-negative bacteria.

In addition, the antibiotics are also as described above, and in particular, may be a polymyxin-based antibiotic.

Therefore, the antimicrobial composition of the present invention may more improve the antimicrobial activity of the polymyxin-based antibiotic against bacteria resistant to the polymyxin-based antibiotic as compared with the case of administering the polymyxin-based antibiotic alone.

In the specific example of the present invention, when bacteria resistant to the polymyxin-based antibiotic are treated with the antimicrobial adjuvant and the polymyxin-based antibiotic in combination, a synergistic effect is shown, thereby having an effect of inhibiting bacterial growth and damaging a cell membrane to derive cell death.

In addition, since the antimicrobial composition of the present invention uses the antimicrobial adjuvant in combination, sufficient antimicrobial activity may be achieved though the polymyxin-based antibiotic is not administered in excess. Therefore, side effects such as nephrotoxicity caused by the administration of an excessive amount of the polymyxin-based antibiotic may be significantly lowered.

In the specific example of the present invention, it was confirmed that when the polymyxin-based antibiotic causing nephrotoxicity and the antimicrobial adjuvant of the present invention are used in combination, nephrotoxicity is not caused in a sepsis animal model, and also a survival rate is improved.

Another aspect of the present invention provides a pharmaceutical composition for preventing or treating organ damage from sepsis or septic shock including an antimicrobial adjuvant including the compound represented by Chemical Formula 1 or a pharmaceutically acceptable salt thereof as an effective component, and an antibiotic as effective components.

The antibiotic is also as described above, and in particular, may be a polymyxin-based antibiotic. The sepsis or septic shock may be caused by gram-negative bacteria, and the gram-negative bacteria are not limited as long as they are resistant to an antibiotic and may be, for example, *Escherichia* sp. and/or *Acinetobacter* sp.

The "sepsis" refers to a condition in which a serious inflammatory response occurs throughout the body due to infection with microorganisms. When two or more symptoms among fever or hypothermia, increased respiratory rate (tachypnea), increased heart rate (tachycardia), and increased or significantly decreased white blood cell count on a blood test are shown, it is referred to as a systemic inflammatory response syndrome (SIRS). When the systemic inflammatory response syndrome is caused by a microbial infection, it is referred to as sepsis. Pathogens continuously or intermittently enter a bloodstream in an infectious focus of the body and settle in various organ tissues to make foci, and a severe systemic symptom is shown, and sepsis is more likely to affect the weak, the elderly, and the debilitated. Sepsis may potentially cause septic shock. When sepsis becomes severe, the functions of various organs (such as heart, kidneys, liver, brain, and lungs) of the body deteriorate, leading to a shock state.

In the specific example of the present invention, it was confirmed that the survival rate of a sepsis animal model is improved and the number of bacteria infected in organs (colony-forming unit, CFU) including liver, lungs, kidneys, and spleen is significantly decreased, and thus, a composition including the antimicrobial adjuvant of the present invention and the polymyxin-based antibiotic is useful for preventing or treating sepsis.

The "prevention" refers to all actions which inhibit sepsis or septic shock or delay the onset thereof by administering the composition according to the present invention.

The "treatment" refers to all actions to ameliorate or favorably change clinical symptoms related to sepsis and conditions related to a multi-organ dysfunction syndrome (for example, fever of various degrees, hypotoxemia, reflex tachycardia, endothelitis, myocardial infarction, high altitude confusion, altered mental state, vascular collapse and organ damage, acute respiratory distress syndrome, coagulopathy, heart failure, renal failure, shock and/or coma, and the like).

In addition, the present invention may inhibit organ damage from sepsis. The pharmaceutical composition of the present invention may prevent or treat sepsis by inhibiting organ damage from sepsis. The organ is an organ damaged by sepsis, and the organ of which the damage is inhibited by the composition of the present invention is not limited, and for example, may be at least one selected from the group consisting of liver, kidneys, and lungs.

The pharmaceutical composition according to the present invention may be formulated by adding a non-toxic and pharmaceutically acceptable carrier, a reinforcement, an excipient, and the like according to a common method, and for example, may be prepared into a preparation for oral administration or a preparation for parenteral administration such as tablets, capsules, troches, liquids, and suspensions.

In addition, an excipient which may be used in the pharmaceutical composition according to the present invention may include sweetening agents, binders, solubilizers, dissolving aids, wetting agents, emulsifiers, tonicity agents, adsorbents, disintegrants, antioxidants, preservatives, lubricants, fillers, fragrance, and the like, and for example, may include lactose, dextrose, sucrose, mannitol, sorbitol, cellulose, glycine, silica, talc, stearic acid, sterin, magnesium stearate, magnesium aluminum silicate, starch, gelatin, gum tragacanth, alginic acid, sodium alginate, methyl cellulose, sodium carboxymethyl cellulose, agar, water, ethanol, polyethylene glycol, polyvinylpyrrolidone, sodium chloride, calcium chloride, orange essence, strawberry essence, vanilla flavor, and the like.

The compound of the present invention may be included at a concentration level in a range of 0.1 wt % to 95 wt %, that is, in a sufficient amount to obtain the effect to be desired, with respect to the total weight of the pharmaceutical composition.

The pharmaceutical composition of the present invention may be administered to mammals such as rats, mice, livestock, and humans by various routes. All modes of administration may be, for example, transdermal, oral, rectal, intravenous, abdominal, intramuscular, subcutaneous, endometrial, or intracerebroventricular injection, and preferably, any one route of oral or intravenous administration, but are not limited thereto.

The administration may include one or more effective components which show the same or similar function. For administration, one or more pharmaceutically acceptable carriers may be further included. The pharmaceutically acceptable carrier may be saline solution, sterile water, Ringer's solution, buffered saline solution, dextrose solution, maltodextrin solution, glycerol, ethanol, and a mixture of one or more of them, and if necessary, other common additives such as antioxidants, buffers, and bacteriostatic agents may be added. In addition, the compound according to the present invention may be easily formulated into various forms, and for example, may be formulated into an injection formulation, such as aqueous solutions, suspensions, and emulsions, powders, tablets, capsules, pills, granules, or injections by further adding diluents, dispersants, surfactants, binders, and lubricants.

The amount of the compound varies over a range depending on the weight, age, gender, health condition, diet, administration time, administration method, excretion rate, disease severity, and the like of patients. A daily dosage of the compound of the present invention is 0.0001 to 100 mg/kg, and preferably an amount of 0.001 to 30 mg/kg may be administered once or several times a day. In addition, an administration period may be one day to two months, but may not be limited until a disease prevention or treatment effect is shown.

Since the antimicrobial adjuvant of the present invention improves the sensitivity of gram-negative bacteria to a polymyxin-based antibiotic, thereby lowering the dosage of the polymyxin-based antibiotic treated for inhibiting gram-negative bacterial growth by up to 128 times, conventional side effects such as nephrotoxicity caused by administering an excessive amount of polymyxin may be significantly lowered, and an excellent bacterial growth inhibition and killing effect is shown, so that the antimicrobial activity of the polymyxin-based antibiotic against the gram-negative bacteria which was resistant to the polymyxin-based antibiotic may be recovered, and thus, the present invention has efficacy of using the conventional antibiotics as they are without a need to separately develop new antibiotics.

Another aspect of the present invention provides a method of preventing, ameliorating, or treating organ damage from sepsis or septic shock including: administering an antimicrobial adjuvant including the compound represented by Chemical Formula 1 or a pharmaceutically acceptable salt thereof as an effective component; and a polymyxin-based antibiotic to an individual.

Another aspect of the present invention provides a use of an antimicrobial adjuvant including the compound represented by Chemical Formula 1 or a pharmaceutically acceptable salt thereof as an effective compound; and the polymyxin-based antibiotic, for using preparation of a drug for preventing, ameliorating, or treating organ damage from sepsis or septic shock.

BEST MODE FOR CARRYING OUT THE INVENTION

Hereinafter, the present invention will be described in detail by the examples and the experimental examples. However, the following examples and experimental examples are only illustrative of the present invention, and do not limit the description of the present invention in any way.

[Example 1] Selection of Compound Which Improves Bacterial Susceptibility to Polymyxin-Based Antibiotic

1-1. Selection of PA108 Compound

In the present invention, a substance which may work with polymyxin to kill polymyxin-resistant bacteria was screened among various compounds owned by the compound bank of the Korea Research Institute of Chemical Technology, using a method of measuring a cellular respiration rate. As the bacteria, bacteria which were separated from sepsis-infected patients at Yonsei University Hospital and identified as *Acinetobacter baumannii* colistin resistance 357 (hereinafter, referred to as R357 strains) which are both a polymyxin-resistant strain and a multidrug-resistant strain were provided and used in the experiment.

Specifically, in a LB agar plate in which bacteria had been grown, a single colony was inoculated into a 3 ml of LB broth and incubated overnight at 220 rpm at 37° C. for 16 hours. Thereafter, 50 ml of a 1/1000 diluted solution of a culture medium was prepared in a 250 ml flask, 0.5% triphenyl tetrazolium chloride (TTC) was added thereto, and 16 μg/mL of polymyxin B (hereinafter, referred to as PMB) was added and mixed. Next, the solution was dispensed at 198 ul each into a 96-well plate, each different candidate compound was finally adjusted to a concentration of 5 μM, dispensed at 2 ul into each well, and mixed, observation was performed at 37° C. for 24 hours using a phenotype microarray, the OD value was measured once more using a multi-functional microplate reader, and the resultant values were compared.

As a result, a compound having an activity to improve bacterial susceptibility to a polymyxin-based antibiotic (compound of the following Chemical Formula 2) was selected, and the compound was named PA108 and used later in the experiment.

[Chemical Formula 2]

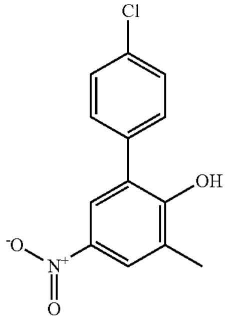

1-2. Confirmation of Activity of PA108 Derivative as Antimicrobial Adjuvant

In order to find structural relevance of the activity of the PA108 compound, a total of 14 PA108 derivatives listed in [Table 1] were prepared, and a synergistic effect of PMB with them was verified by a method of measuring a bacterial respiration rate. PA108 derivatives were provided from the compound bank of the Korea Research Institute of Chemical Technology or directly synthesized.

Specifically, in a LB agar plate in which bacteria had been grown, a single colony was inoculated into a 3 ml of LB broth and incubated overnight at 220 rpm at 37° C. for 16 hours. Thereafter, 50 ml of a 1/1000 diluted solution of a culture medium was prepared in a 250 ml flask, 0.5% triphenyl tetrazolium chloride (TTC) was added thereto, and 16 μg/mL of polymyxin B (PMB) was added and mixed. Next, the solution was dispensed at 198 ul each into a 96-well plate, each different candidate compound was finally adjusted to a concentration of 5 μM, dispensed at 2 ul into each well, and mixed, observation was performed at 37° C. for 24 hours using a phenotype microarray, the OD value was measured once more using a multifunctional microplate reader, and the resultant values were compared.

As a result, any significant effect of killing R357 strains was not shown in derivatives other than the original PA108 (FIG. 1).

TABLE 1

| Compound Name | Chemical Structure | Compound Name | Chemical Structure |
|---|---|---|---|
| PA108-1 | 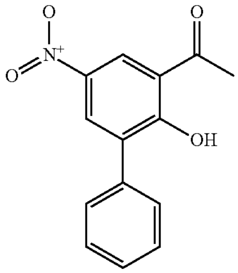 | PA108-2 | 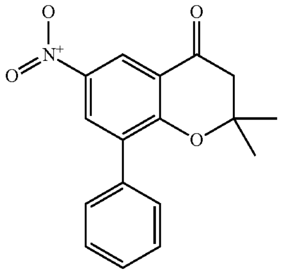 |
| PA108-3 | 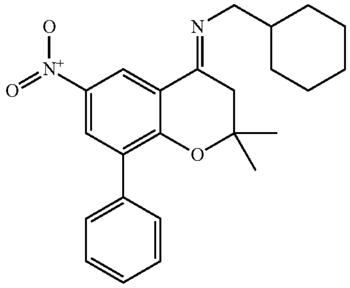 | PA108-4 | 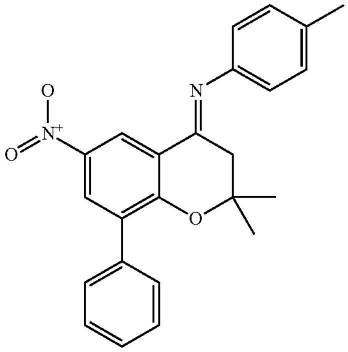 |

TABLE 1-continued
| Compound Name | Chemical Structure | Compound Name | Chemical Structure |
| --- | --- | --- | --- |
| PA108-5 | 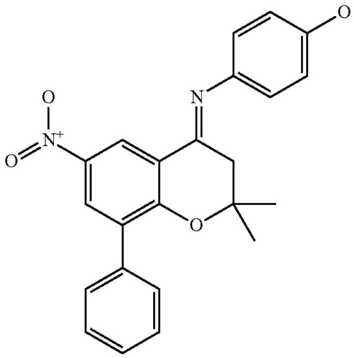 | PA108-6 | 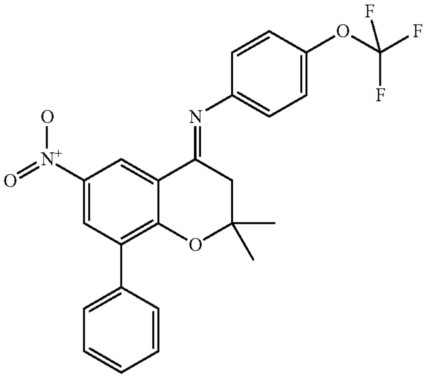 |
| PA108-7 | 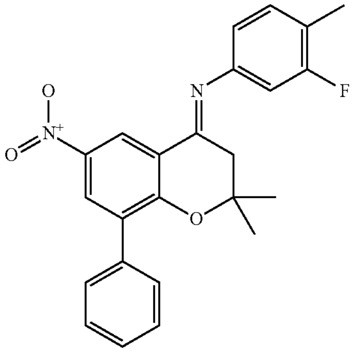 | PA108-8 | 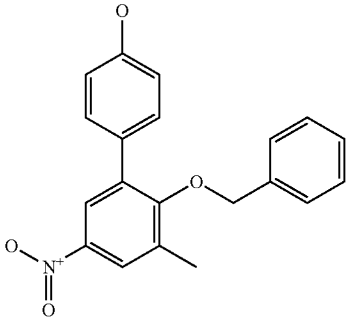 |
| PA108-9 | 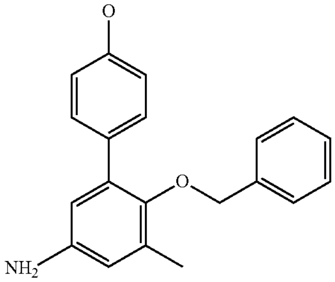 [SMILES: Cc1cc(N)cc(-c2ccc(O)cc2)c1OCc1ccccc1] | PA108-10 | 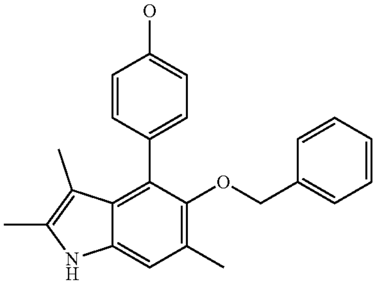 [SMILES: Cc1cc2[nH]c(C)c(C)c2c(-c2ccc(O)cc2)c1OCc1ccccc1] |
| PA108-11 | 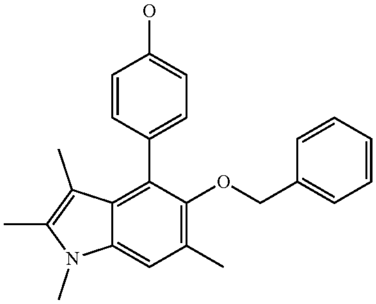 [SMILES: Cc1cc2c(c(C)c(C)n2C)c(-c2ccc(O)cc2)c1OCc1ccccc1] | PA108-12 | 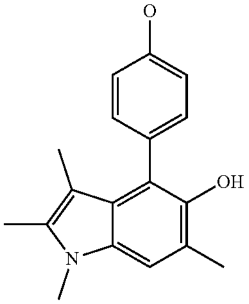 [SMILES: Cc1cc2c(c(C)c(C)n2C)c(-c2ccc(O)cc2)c1O] |

TABLE 1-continued

| Compound Name | Chemical Structure | Compound Name | Chemical Structure |
|---|---|---|---|
| PA108-13 | 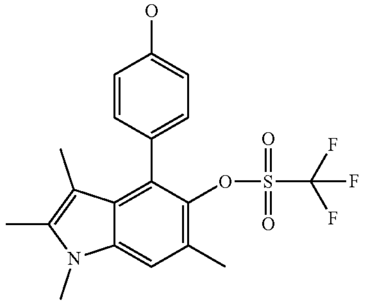 [SMILES: Cc1cc2c(c(C)c(C)n2C)c(-c2ccc(O)cc2)c1OS(=O)(=O)C(F)(F)F] | PA108-14 | 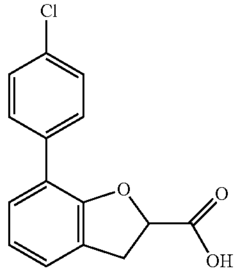 [SMILES: O=C(O)C1Cc2cccc(-c3ccc(Cl)cc3)c2O1] |

[Example 2] Confirmation of Bacterial Growth Inhibitory Effect of PA108

In order to confirm the antimicrobial activity of PA108, a cellular respiration rate was measured by the method used in Example 1, thereby confirming the bacterial growth inhibition effect.

First, in a LB agar plate in which bacteria had been grown, a single colony was inoculated into a 3 ml of LB broth and incubated overnight at 220 rpm at 37° C. for 16 hours. Thereafter, 50 ml of a 1/1000 diluted solution of a culture medium was prepared in a 250 ml flask, 0.5% triphenyl tetrazolium chloride (TTC) was added thereto and mixed. Next, the solution was dispensed at 198 ul each into a 96-well plate. 16 μg/mL of PMB and 5 μM of PA108 were dispensed at 2 ul each so that the concentrations of PMB (16 μg/mL) and PA108 (5 μM) were adjusted into three wells each for 3 repetitions for each treatment and mixed, observation was performed at 37° C. for 24 hours using a phenotype microarray, the OD value was measured once more using a multifunctional microplate reader, and the resultant values were compared.

Figure 2:
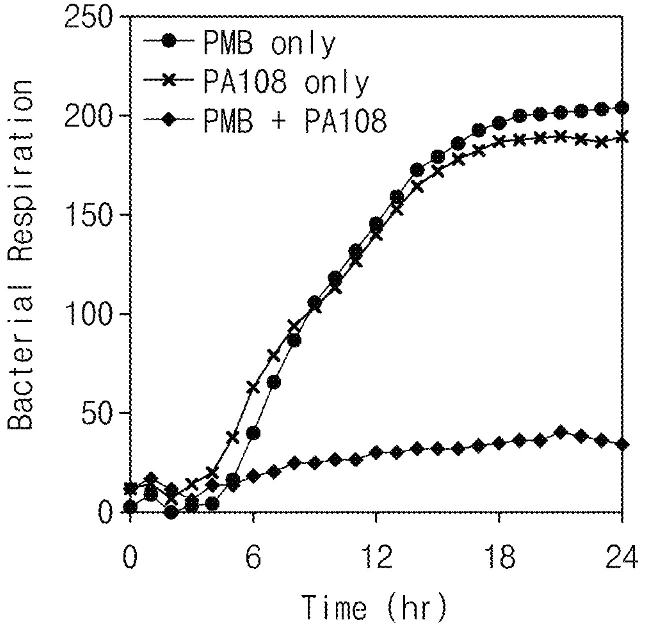
FIG. 2 is a graph showing a bacterial growth inhibitory effect of a treatment with polymyxin B (PMB) alone, PA108 alone, or polymyxin B (PMB) and PA108 in combination on *Acinetobacter baumannii* strains through a bacterial relative respiration rate.

As a result, since the R357 strains had a minimal inhibitory concentration (MIC) of 64 μg/mL against PMB, it was confirmed that it had no cell growth inhibitory effect at a low concentration of 16 μg/mL (FIG. 2, black). In addition, it was confirmed that PA108 which is a developed polymyxin-based antimicrobial adjuvant also had no self cell growth inhibitory effect at a concentration of 5 μM (FIG. 2, blue). However, when a treatment was performed with both PMB and PA108, it was confirmed that cellular respiration was effectively inhibited (FIG. 2, red).

[Example 3] Confirmation of Cell Death Effect Increased by PA108

Antibiotics have two efficacies largely. There are a bacteriostatic which inhibits bacterial growth without bacterial death and a bactericidal which causes bacterial death. In order to confirm whether a sterilization effect was actually increased when a treatment with PA108 with polymyxin was performed, a bacterial viability test was performed.

First, in a LB agar plate, a single colony was inoculated into a 3 ml of a LB broth and incubated overnight under the conditions of 37° C. and 220 rpm for 16 hours. Thereafter, 1% of the culture medium was diluted in a 250 ml Erlenmeyer flask and then incubated to OD=0.5. The grown culture medium was dispensed at 3 ml each into three 15 ml round culture tubes, three treatment groups to which 16 μg/mL of PMB, 5 μM of PA108, and PMB (16 μg/mL) and PA108 (5 μM) were added, respectively were made and dispensed, and 100 ul each was smeared on three LB agar plates per one treatment group every 1, 4, 7, and 12 hours while performing incubation at 220 rpm at 37° C., thereby confirming a colony forming unit (CFU).

Figure 3:
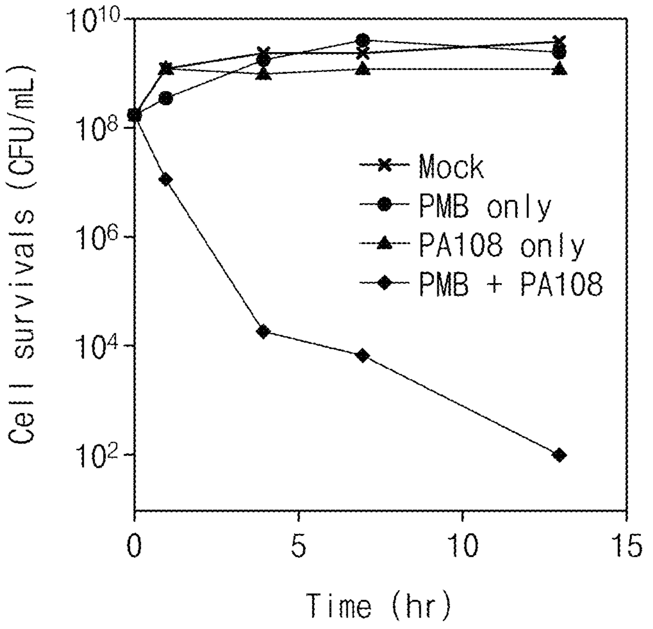
FIG. 3 is a graph showing a cell death effect of a treatment with polymyxin B (PMB) alone, PA108 alone, or polymyxin B (PMB) and PA108 in combination on *Acinetobacter baumannii* strains.

As a result, like the results of the cellular respiration rate, the single treatment group with PMB or PA108 did not show the effect of killing R357b strains (FIG. 3, black, blue). However, it was confirmed in the simultaneous treatment group with both PMB and PA108 that cell death was derived (FIG. 3, red). Furthermore, it was confirmed that the simultaneous treatment group showed 107 times the killing effect of the control group and the single treatment group based on 14 hours, and finally showed a bacterial killing effect of 99.99999%.

[Example 4] Confirmation of Synergistic Antimicrobial Effect of Polymyxin-Based Antibiotic and PA108

In order to confirm whether a synergistic effect was shown when a treatment with PA 108 in combination with a polymyxin-based antibiotic was performed, a checkerboard assay was performed, and a fractional inhibitory concentration index (FICI) was determined from the results.

First, in a LB agar plate, 3-4 colonies were inoculated into a 4-5 ml of a LB broth and incubated overnight at 37° C. and 220 rpm for 16 hours. Thereafter, 5 ml of a 1/10000 dilution of the culture medium was made and incubated to OD=0.08-0.1 at 37° C. and 220 rpm in a 15 ml round culture tube. Next, the solution was diluted to 1/20 and dispensed at 196 ul each into a 96-well plate, PA108 and PMB were dispensed at 2 ul at concentrations of 0-160 μM and 0-64 μg/Ml, respectively and mixed, incubated at 37° C. for 18 hours, in each well, and the OD value was measured using a multifunctional microplate reader.

Next, in order to confirm the synergistic effect, a fractional inhibitory concentration (FIC) index which evaluates the effect on the efficacy of a combination of the compound with the antibiotic by comparing the MIC value with that of the single treatment with the compound was calculated using a standard equation of Compound A single combination/combination of MIC of Compound A+Compound B alone/MIC of Compound B=FIC A+FIC B=FIC Index. MIC and FICI values are shown in Table 2.

It was determined that when the FICI value was 0.5 or less, the effect was synergistic, when the value was 0.5 to 4.0, the effect was indifferent, and when the value was 4 or more, the effect was antagonistic.

TABLE 2

| | | MIC | | | | |
|---|---|---|---|---|---|---|
| Strain | Agent | Alone | Combi | FIC | FICI | Interpretation |
| *A. baumannii* | PB (μg/ml) | 54 | 2 | 0.031 | 0.06225 | Synergy |
| colistin R357 | PA108 (μM) | 160 | 5 | 0.03125 | | |

Figure 4:
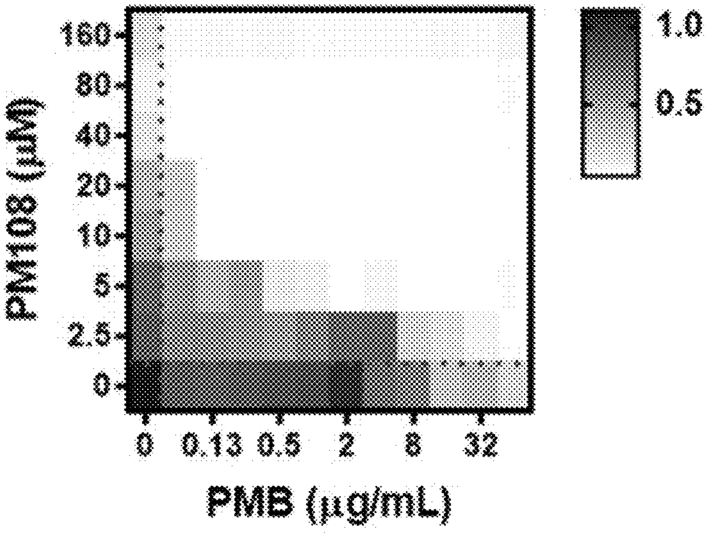
FIG. 4 shows results of confirming whether a synergistic effect on *Acinetobacter baumannii* strains was shown by a treatment with polymyxin B (PMB) and PA108 in combination, through checkerboard analysis.

As a result, it was confirmed that since the FICI value of PA108 and PMB was 0.093, the resistant bacterial killing effect was a synergistic effect (FIG. 4).

[Example 5] Confirmation of Morphological Cell Death Effect of Polymyxin-Based Antibiotic and PA108

In order to confirm the bacterial morphological change when a treatment with PA108 in combination with a polymyxin-based antibiotic was performed, the bacterial morphological change was observed using a fluorescence microscope and a scanning electron microscope.

First, in a LB agar plate, a single colony was inoculated into 3 ml of a LB broth and incubated overnight at 37° C. and 220 rpm for 16 hours. Thereafter, 1% of the culture medium was diluted in a 250 ml of Erlenmeyer flask and incubated to OD=0.5, treated with PMB and PA108 at concentrations of 16 μg/ml and 5 μM, respectively, and incubated for 9 hours. The cells were centrifuged at 4° C. for 10 minutes at 8,000×g, washed three times, and resuspended in PBS. 3 ml of the cell suspension was fixed and then observed with a scanning electron microscope. A LIVE/DEAD BacLight bacterial viability kit (Cat #. L7007, Invitrogen, Waltham, Massachusetts, USA) was used to add SYTO9 (67 mM, 3 μL) which bound to DNA and RNA of living cells to emit green fluorescence and Propidium iodide (PI) (1.67 mM, 3 μL) which bound to DNA and RNA of dead cells to emit red fluorescence to add each sample at a final volume of 3 ml, and the samples were incubated in a dark room at room temperature for 15 hours and observed with a fluorescence microscope.

Figure 5:
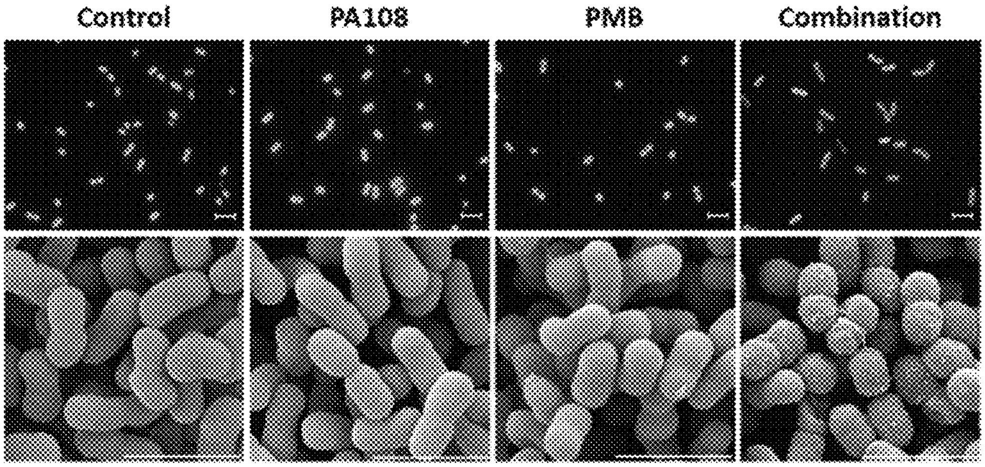
FIG. 5 is photographs in which morphological changes in bacteria were observed under a fluorescence microscope (top) and a scanning electron microscope (bottom), when a treatment was performed with polymyxin B (PMB) alone, PA108 alone, or polymyxin B (PMB) and PA108 in combination against *Acinetobacter baumannii* strains.

As a result, in the observation using the fluorescence microscope, green fluorescence was observed in the single treatment group of PMB or PA08, and thus, it was confirmed that the cells did not die like the control group. However, red fluorescence was observed in the simultaneous treatment group with PMB and PA108, and thus, it was confirmed that cell death was derived (FIG. 5, top)

In addition, in the observation using a scanning electron microscope, it was confirmed that the single treatment group with PMB or PA08 showed an intact form in which the surface of cells was not damaged like the control group. However, it was confirmed that in the simultaneous treatment group with PMB and PA108, cells shrunk and an intracellular substance was leaked, so that the shape and structure of cells were damaged (FIG. 5, bottom).

[Example 6] Confirmation of Nephrotoxicity of PA108

Since the polymyxin-based antibiotic is known to have nephrotoxicity, nephrotoxicity, nephrotoxicity to PMB and PA108 was measured using human body-derived renal cells ACHN (ATCC® CRL-1611™).

First, ACHN renal cells were incubated with $2\times10^4$ cells/well for 24 hours, and the medium was changed to a medium in which PMB or PA108 was mixed in all wells. After 0, 24, 48, 72, and 96 hours of the treatment with PMB or PA108, cell viability was measured as ratios of the amounts of ATP at each time to 0 hour through cell titer glo to evaluate cytotoxicity.

Figure 6:
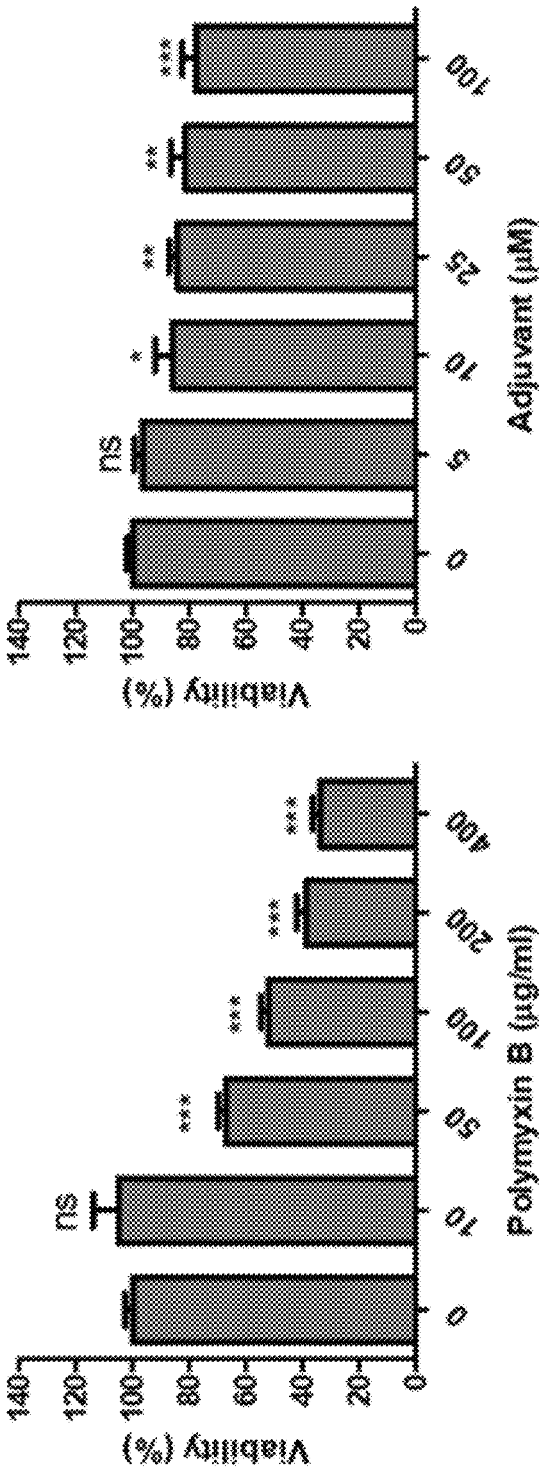
FIG. 6 shows nephrotoxicity of polymyxin B (left) and PA108 (right) in human-derived renal cells through renal cell viability.

As a result, it was confirmed that in the case of PMB, the viability of renal cells decreased from a concentration of 50 μg/mL (FIG. 6, left). In the case of polymyxin-based antibiotic-resistant strains R357, since a minimum inhibitory concentration by polymyxin was 64 μg/mL, it was expected that nephrotoxicity would be shown at a concentration of 64 μg/mL at which a therapeutic effect is shown in R357 infection. However, in the case of PA108, it was confirmed that nephrotoxicity was not shown at all at a working concentration of 5 μM, and renal cells showed viability of 80% or more even at a higher concentration, unlike PMB (FIG. 6, right). Therefore, when the treatment was performed with both PMB and PA108, a sterilization effect on polymyxin-based antibiotic-resistant strains R357 was shown even at 16 μg/mL of PMB, and thus, it was expected that when the treatment was performed with PMB and PA108 in combination, nephrotoxicity would not be shown.

[Example 7] Confirmation of Survival Rate by Treatment with PA108 in Mouse Sepsis Model It was confirmed whether the simultaneous treatment with PA108 and PMB was effective for treating sepsis caused by R357 infection in a polymyxin-based antibiotic-resistant strains R357-infected mouse model.

Specifically, $5\times10^7$ of R357 strains were intraperitoneally injected into 6 week old C57BL/6 mouses to prepare a sepsis mouse model caused by R357 infection, and PMB at a dose of 100 μg/kg and PA108 at a dose of 60 μg/kg were intraperitoneally injected alone or in combination to measure the survival rate of the mouse.

Figure 7:
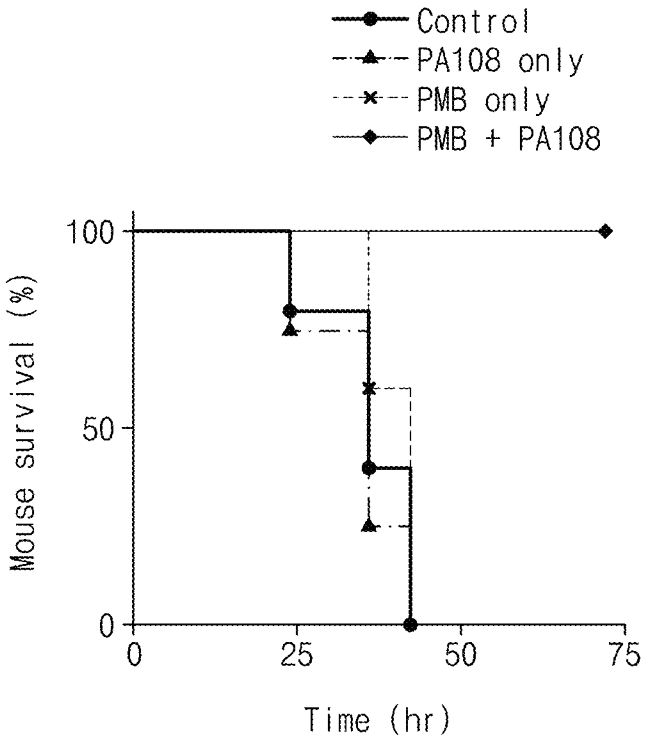
FIG. 7 shows a mouse survival rate by administration of polymyxin B (PMB) alone, PA108 alone, or polymyxin B (PMB) and PA108 in combination in a mouse sepsis model due to infection with *Acinetobacter baumannii* strains.

As a result, it was confirmed that all of the mouses died within 42 hours in a control group, a PMB single treatment group, and a PA108 single treatment group. However, in the case of the simultaneous treatment group with PMB and PA108, the mouse was alive until 168 hours without showing any pathological symptoms (FIG. 7). In addition, as a result of autopsy of the mouse of the simultaneous treatment group with PMB and PA108, R357 strains were not detected in organs of the mouse, and thus, it was confirmed that R357 strains were completely removed by the simultaneous treatment with PMB and PA108.

[Example 8] Confirmation of Efficacy as Antimicrobial Adjuvant in Other Species of Polymyxin-Resistant Bacteria In order to confirm whether a synergistic effect was shown when polymyxin-resistant bacteria of species other than R357 strains were treated with PA108 and the polymyxin-based antibiotic simultaneously, a checkerboard assay was performed, and a fractional inhibitory concentration index (FICI) was determined from the results.

First, in each LB agar plate in which bacteria (*Klebsiella pneumonia* SCH530, SCH740, SCH777, *Pseudomonas aeruginosa* SMC-U9, SMC-U10, SMC-U11) were grown, 3 to 4 colonies were inoculated into 4 to 5 ml of a LB broth and incubated overnight at 220 rpm at 37° C. for 16 hours. The next day, 5 ml of a culture medium diluted to 1/10000 was incubated to OD=0.08-0.1 in a 15 ml round culture tube at 220 rpm at a temperature of 37° C., and was diluted to 1/20 and dispensed at 196 ul in a 96-well plate. PA108 and PMB were dispensed at concentrations of 0 to 80 μM and 0 to 128 μg/Ml, respectively at 2 ul each and mixed in each well, and incubated at 37° C. for 18 hours to measure the OD value using a multifunctional microplate reader.

Next, FICI was calculated in the same manner as in Example 4, and the MIC and FICI values are shown in the following Table 3:

TABLE 3

| | | MIC | | | | |
|---|---|---|---|---|---|---|
| Strain | Agent | Alone | Combi | FIC | FICI | Interpretation |
| *K. pneumoniae* SCH530 | P8 (μg/ml) | 8 | 0.5 | 0.0623 | 0.094 | Synergy |
| | PA108 (μM) | 160 | 5 | 0.03125 | | |
| *K. pneumoniae* SCH740 | P8 (μg/ml) | 128 | 1 | 0.00781 | 0.039 | Synergy |
| | PA108 (μM) | 160 | 5 | 0.03125 | | |
| *K. pneumoniae* SCH777 | P8 (μg/ml) | 128 | 0.5 | 0.00391 | 0.035 | Synergy |
| | PA108 (μM) | 160 | 5 | 0.03125 | | |
| *P. aeruginosa* SMC-U9 | P8 (μg/ml) | 16 | 4 | 0.25 | 0.313 | Synergy |
| | PA108 (μM) | 160 | 10 | 0.0625 | | |
| *P. aeruginosa* SMC-U10 | P8 (μg/ml) | 16 | 2 | 0.125 | 0.188 | Synergy |
| | PA108 (μM) | 160 | 10 | 0.0625 | | |
| *P. aeruginosa* SMC-U11 | P8 (μg/ml) | 32 | 2 | 0.0625 | 0.125 | Synergy |
| | PA108 (μM) | 160 | 10 | 0.0625 | | |

Figure 8:
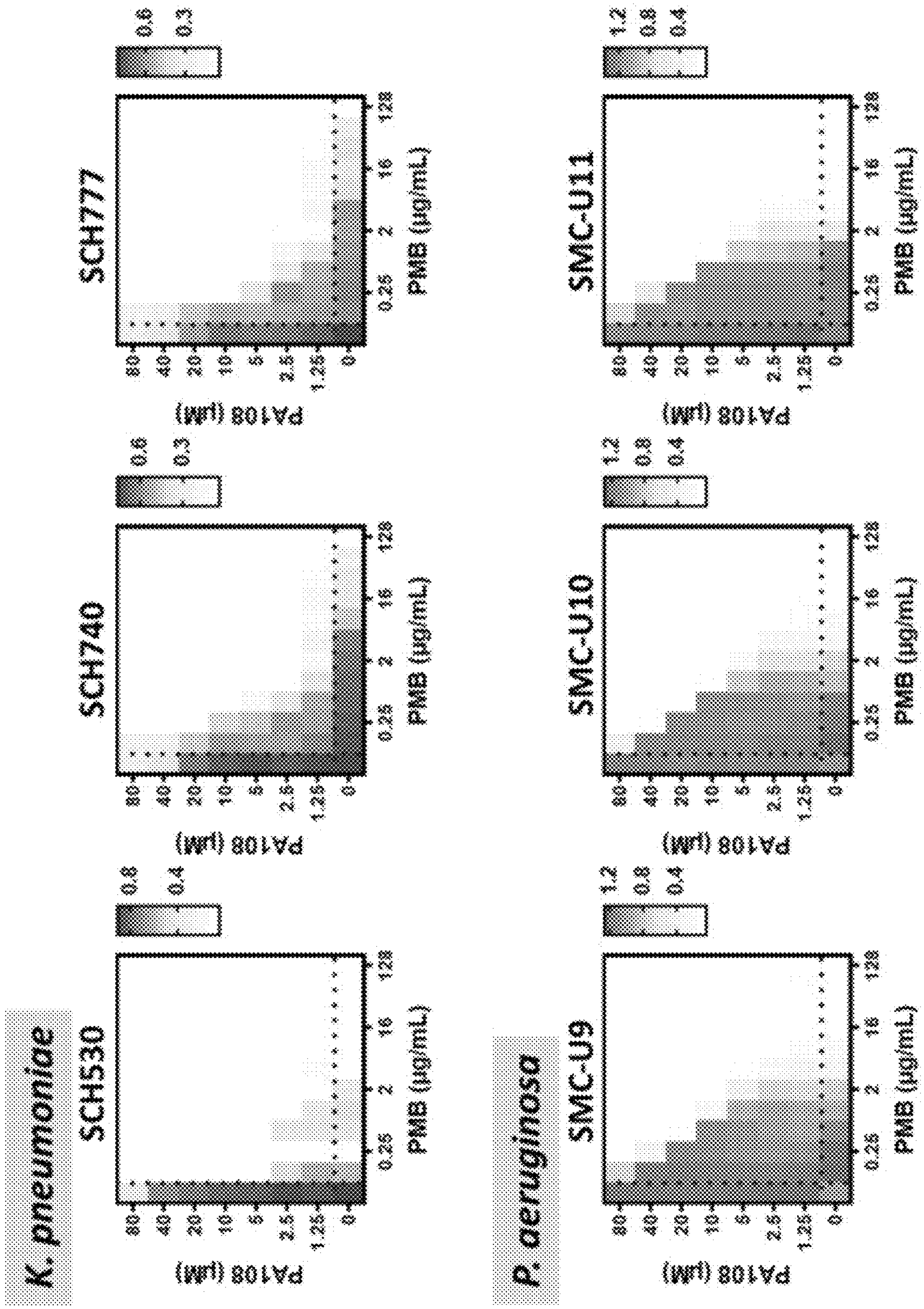
FIG. 8 shows results of confirming whether a synergistic effect on three *Klebsiella pneumoniae* strains and three *Pseudomonas aeruginosa* strains which show resistance to a polymyxin-based antibiotic was shown by a treatment with polymyxin B (PMB) and PA108 in combination, through checkerboard analysis.

As a result, since the FICI value of PA108 and PMB was shown to be 0.5 or less which is a reference value showing a synergistic effect in all strains, it was confirmed that the effect of killing other species of gram-negative bacteria (*Klebsiella pneumonia* SCH530, SCH740, SCH777, *Pseudomonas aeruginosa* SMC-U9, SMC-U10, SMC-U11) is the synergistic effect of PA108 and PMB (FIG. 8).

[Example 9] Confirmation of Change in Gene Expression and Mechanism of Action by Simultaneous Treatment with Polymyxin-Based Antibiotic and PA108

A change in expression of main genes involved in the death of resistant bacteria when a treatment with PA108 in combination with the polymyxin-based antibiotic PMB was performed was confirmed by transcriptome analysis.

First, in a LB agar plate, a single colony was inoculated into a 3 ml of a LB broth and incubated overnight under the conditions of 37° C. and 220 rpm for 16 hours. Thereafter, 1% of the culture medium was diluted in a 250 mL Erlenmeyer flask and then incubated to OD=0.5. The culture medium was dispensed at 5 ml each into three 15 ml round culture tubes, treated with PMB at a concentration of 16 μg/ml, PA108 at a concentration of 5 μm, and PMB at a concentration of 16 μg/ml and PA108 at a concentration of 5 μm, respectively, and incubated at 37° C. and 220 rpm for 1 hour. Thereafter, bacteria were washed three times with PBS, centrifuged at 4° C. and 8,000×g for 10 minutes, and stored at −80° C.

The library for performing RNA sequencing was prepared by extracting total RNA with a TruSeq Stranded Total RNA sample preparation kit including Ribo-Zero H/M/R, and synthesizing 150 bp-sized cDNA. The quality of the synthesized cDNA library was evaluated by Agilent 2100 BioAnalyzer (Agilent, CA, USA), and after amplifying the cluster of a denatured template, paired-end sequencing which sequences both ends of a DNA fragment using Illumina Novaseq 6000 (Illumina, CA, USA) was performed. For transcriptomic data analysis, the read value was filtered, and the filtered read value was mapped to a reference genome using an aligner STAR v.2.4.0b. Thereafter, in order to measure a gene expression amount, gene expression was quantified using a KAPA library quantification kit (Kapa Biosystems, MA, USA) according to the library quantification protocol of the manufacturer.

In order to identify a differential expression gene (DEG), a gene expression level was measured with Cufflinks v2.1.1 using gene annotation database, and gene expression level count data was produced using HTSeq-count v0.6.1p1. Form the produced data, a TCC R package was used to identify a gene having a q value of less than 0.05 as a differential expression gene.

For the genes identified as the differential expression gene (DEG), gene ontology (GO) analysis in which genes were classified according to three categories of biological process, molecular function, and cellular component, and information about the function of genes is provided was performed.

Figure 9:
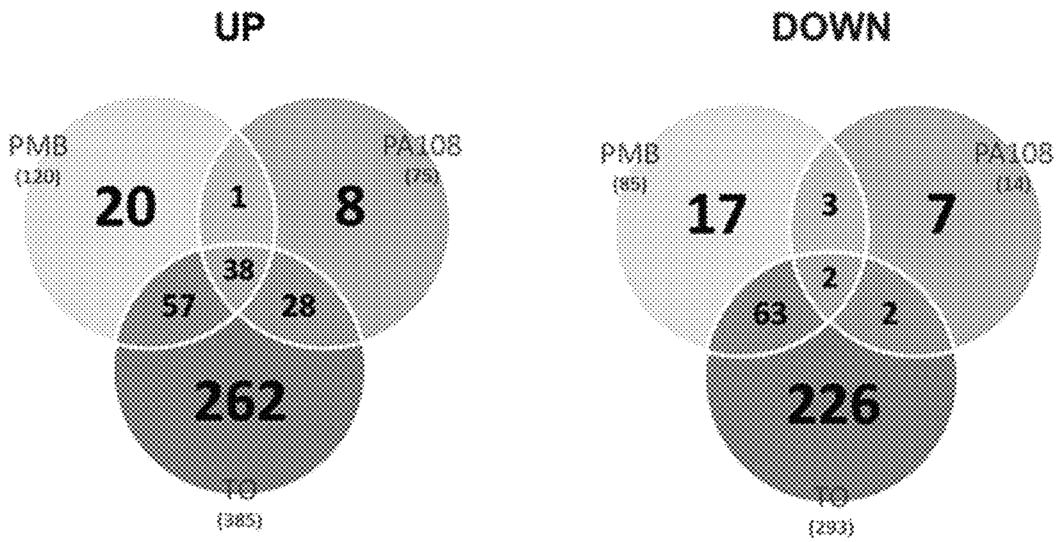
FIG. 9 shows the number of genes having increased expression (left) and the number of genes having decreased expression (right) as compared with a control group, when a treatment was performed with polymyxin B (PMB) alone, PA108 alone, or polymyxin B (PMB) and PA108 in combination against *Acinetobacter baumannii* strains.
Figure 10:
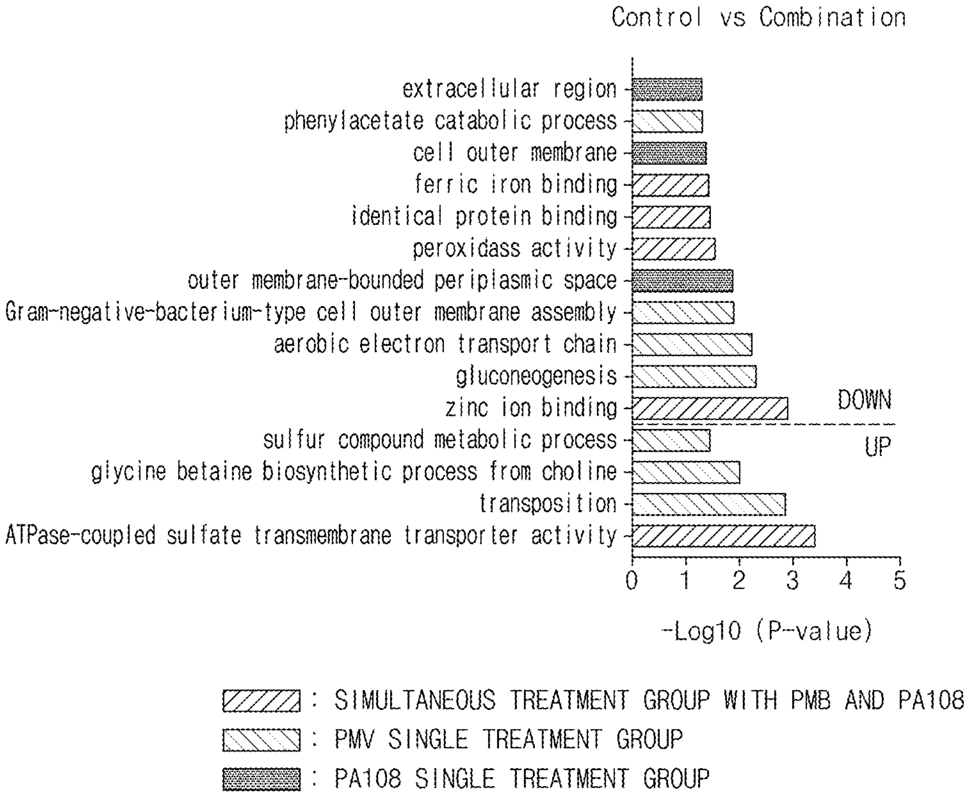
FIG. 10 shows functional information of genes having high statistical significance among genes having increased or decreased expression as compared with a control group when a treatment with polymyxin B (PMB) and PA 108 in combination was performed (purple: group treated with PMB and PA108 in combination, yellow: group treated with PMB, blue: group treated with PA 108).

As a result, as compared with the control group, significant gene change was observed in all of the PMB single treatment group, the PA108 single treatment group, and the simultaneous treatment group with PMB and PA108 (FIG. 9). In addition, it was confirmed from gene ontology (GO) analysis that when the simultaneous treatment with PMB and PA108 was performed, expression of genes involved in zinc ion binding, identical protein binding, and ferric ion binding and expression of genes involved in peroxidase activity may be significantly decreased, and expression of genes involved in transport of substances through a cell membrane, in particular, ATPase-coupled sulfate transmembrane transporter activity was significantly increased (FIG. 10).

It is presumed that when the treatment was performed with a low dose of antibiotic PMB, a physical and chemical environment in which external substance may penetrate more easily is created, and as PA108 penetrates more easily to a periplasmic space, expression of genes related to the function of a cell membrane in charge of oxidation of protein and transportation of various nutrients is decreased and a cell death effect is shown.

In addition, it is presumed therefrom that a intracellular oxidation stress reaction is caused by superoxide which is an active oxygen showing high mutation rate and growth defects and acting as a toxin and hydrogen peroxide, and the expression of genes related to the activity of active oxygen regulating enzymes to regulate the reaction is decreased to disrupt cellular homeostasis, and thus, a cell death effect is shown.

Additionally, it is presumed that expression of genes related to iron ion bonding and a proteolytic function and genes related to phenylacetate catabolism is inhibited to inhibit sideropore synthesis, and PMB and PA108 which have passed through the cell membrane bind to certain protein and DNA to lower a metabolism and show a cell death effect.

The antimicrobial composition of the present invention has smooth fluidity of the cell membrane by a treatment with a low concentration of antibiotic (PMBB) which does not have a direct effect on bacteria, and the bacterial active oxygen is excessively produced by a substance (PA108) entering the cyoplasm to disrupt cellular homeostasis and as a result, decrease cell permeability to derive cell death.

[Example 10] Confirmation of Change in Bacterial Membrane by Simultaneous Treatment with Polymyxin-Based Antibiotic and PA108

Polymyxin E (colistin) binds specifically to phospholipid and lipopolysaccharide (LPS) in the outer cell membrane of gram-negative bacteria to show sterilization activity, and colistin-resistant bacteria has decreased affinity between colistin and bacterial outer membrane due to modified LPS to show resistance to colistin. Therefore, it was confirmed whether the addition of PA108 caused a change in bacterial translocation and permeability.

Specifically, for sample preparation, a colony culture grown for 16 hours was washed and resuspended in 0.01 M PBS at pH 7.4. Absorbance at 600 nm in a bacteria suspension was standardized to 0.5 in the same buffer solution, and a pigment PI9 (cat. P1304MP, Thermo Fisher Scientific, Waltham, Massachusetts, USA) was added at a final concentration of 1.67 μM. After incubation at 37° C. for 30 minutes, 198 μl of fluorescently labeled bacteria cells were added to a 96-well plate, and 16 μg/ml of PMB and 2 μl of 5 μM PA108 were added. After incubation for 30 minutes again, fluorescence was measured in a fluorescence measurement wavelength range of excitation of 535 nm and emission of 615 nm by a multifunctional microplate reader to measure membrane permeability.

The cell membrane potential was resuspended in 5 mM HEPES (pH 7.0, +5 mM of glucose), DiSC3(5) (3,3'-Dipropylthiadicarbocyanine Iodide) (50 μM, Cat. D306, Invitrogen, Carlsbad, California) which is a pigment sensitive to potential was added, incubation was performed for 30 minutes, and then fluorescence was measured by a multifunctional microplate reader to measure membrane potential.

Figure 11:
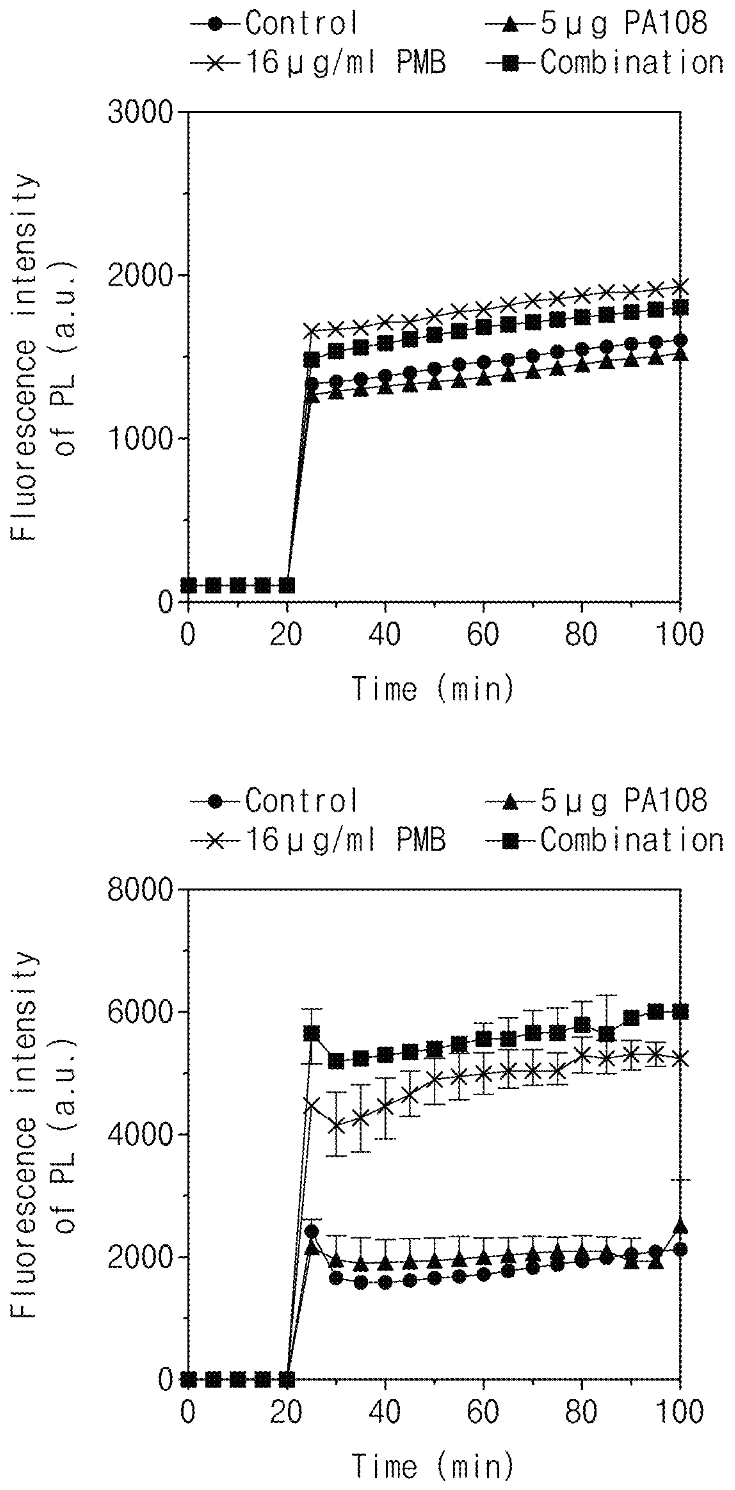
FIG. 11 shows changes in cell membrane permeability (left) and changes in cytoplasmic membrane potential (right) of bacteria, when a treatment was performed with polymyxin B (PMB) alone, PA108 alone, or polymyxin B (PMB) and PA108 in combination against *Acinetobacter baumannii* strains.

As a result, it was confirmed that the treatment with PMB and PA108 in combination changed the bacterial cytoplasmic membrane potential (FIG. 11, right), but did not affect the overall membrane permeability (FIG. 11, left).

The results suggest that the treatment with a low dose of PMB did not change in membrane permeability which leads to the bacterial death, but formed a physical and chemical environment in which lipopolysaccharide (LPS) in the outer membrane of gram-negative bacteria was destabilized and foreign substances entered more easily, and simultaneously treated PA108 entered the cell membrane and formed the ion channel or pores of the cell membrane to derive high membrane depolarization of the cell membrane.

As a result, it is shown that PA108 is treated simultaneously as the antimicrobial adjuvant to PMB to cause a damage of a lipid bilayer region of bacterial cell plasma membrane to serve to derive bacterial death.

The invention claimed is:

1. A method of improving a bactericidal effect of an antibiotic in a subject in need thereof, comprising administering to the subject in need thereof, in combination with the antibiotic, a composition comprising a compound of the Chemical Formula 1 or a pharmaceutically acceptable salt thereof:

[Chemical Formula 1]

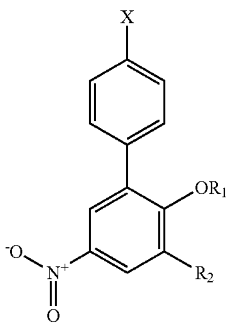

wherein

X is a halogen atom, and $R_1$ and $R_2$ are independently of each other a hydrogen atom or alkyl having 1 to 6 carbon atoms.

2. The method of claim 1, wherein X is a chlorine atom, $R_1$ is a hydrogen atom, and $R_2$ is methyl.

3. The method of claim 1, wherein the composition improves bacterial susceptibility to a polymyxin-based antibiotic.

4. The method of claim 3, wherein the polymyxin-based antibiotic is polymyxin B or polymyxin E.

5. The method of claim 3, wherein the bacteria are gram-negative bacteria.

6. The method of claim 5, wherein the gram-negative bacteria are *Escherichia* sp., *Acinetobacter* sp., *Pseudomonas* sp., or *Klebsiella* sp.

7. The method of claim 6, wherein the *Escherichia* sp. is at least one selected from the group consisting of *Escherichia coli, Escherichia albertii, Escherichia blattae, Escherichia fergusonii, Escherichia hermannii*, and *Escherichia vulneris,* the *Acinetobacter* sp. is at least one selected from the group consisting of *Acinetobacter baumannii, Acinetobacter junii, Acinetobacter boissieri, Acinetobacter calcoaceticus, Acinetobacter haemolyticus, Acinetobacter nosocomialis, Acinetobacter schindleri*, and *Acinetobacter ursingii,* the *Pseudomonas* sp. is at least one selected from the group consisting of *Pseudomonas aeruginosa; Pseudomonas fluorescens, Pseudomonas putida, Pseudomonas chlororaphis, Pseudomanas pertucinogena, Pseudomanas stutzeri*, and *Pseudomanas syringae*, and the *Klebsiella* sp. is at least one selected from the group consisting of *Klebsiella pneumonia, Klebsiella granulomatis, Klebsiella oxytoca*, and *Klebsiella terrigena.*

8. The method of claim 5, wherein the gram-negative bacteria are polymyxin-based antibiotic-resistant bacteria or multidrug-resistant bacteria.

9. The method of claim 1, wherein the antibiotic is a polymyxin-based antibiotic.

10. The method of claim 9, which derives cell death of gram-negative bacteria.

11. The method of claim 9, which derives cell membrane depolarization of the gram-negative bacteria to damage the cell membrane.

12. The method of claim 1, wherein the subject in need has a risk of developing organ damage from sepsis or septic shock.

13. The method of claim 12, wherein the sepsis or the septic shock is caused by infection with bacteria of *Escherichia* sp. or *Acinetobacter* sp.

14. The method of claim 12, wherein the organ is at least one selected from the group consisting of liver, kidneys, and lungs.

* * * * *